United States Patent [19]
Liang et al.

[11] Patent Number: 5,872,206
[45] Date of Patent: Feb. 16, 1999

[54] COMPOSITIONS AND METHODS FOR INTERFERING WTIH HEPATITIS B VIRUS INFECTION

[75] Inventors: Tsanyang Jake Liang, Brookline; Jiakang Huang, Cambridge, both of Mass.

[73] Assignee: The General Hospital Corporation, Boston, Mass.

[21] Appl. No.: 319,376

[22] Filed: Oct. 6, 1994

[51] Int. Cl.$^6$ .............................. A61K 38/00; C07K 2/00
[52] U.S. Cl. ..................... 530/300; 530/324; 530/326; 530/350; 530/412
[58] Field of Search ................... 435/5, 6, 69.1, 435/70.1, 71.1, 71.2, 320.1, 252.3; 436/501, 300; 530/350, 324, 412, 326; 536/23.72

[56] References Cited

U.S. PATENT DOCUMENTS

| | | | |
|---|---|---|---|
| 4,777,240 | 10/1988 | Moriarty et al. | 530/326 |
| 5,204,446 | 4/1993 | Kumazawa et al. | |
| 5,425,942 | 6/1995 | Tanaka | 424/94.1 |

FOREIGN PATENT DOCUMENTS

| | | | |
|---|---|---|---|
| 4077497 | 3/1992 | Japan . | |
| 7255476 | 10/1995 | Japan . | |
| 9102278 | 12/1991 | WIPO | C07K 13/00 |
| WO 92/11289 | 12/1991 | WIPO . | |
| 9203914 | 5/1992 | WIPO | C12N 15/57 |

OTHER PUBLICATIONS

Fischer et al., *Virus Genes* 10:1, 99–102 (995).
Huang et al., *AASLD Abstracts: Hepatology* vol. 20(4), p. 305A Abstract 833 (1994).
Fischer et al., "HBx Protein of Hepatitis B Virus Interacts with the C–Terminal Portion of a Novel Human Proteasome Alpha–Subunit", Virus Genes 10, 99–102, 1995.

Maguire et al., "HBV X Protein Alters the DNA Binding Specificity of CREB and ATF–2 by Protein–Protein Interactions", Science 252, 842–844, 1991.

Rock et al., "Inhibitors of the Proteasome Block the Degradation . . . ", Cell 78:761–771, Sep. 9, 1994.

Fehling et al., "MHC Class I Expression in Mice Lacking the Proteasome Subunit LMP–7", Science 265:1234–1237, Aug. 26, 1994.

Pugh et al., "Expression of the X Gene of Hepatitis B Virus", J. Med. Virol. 20:229–246 (1989).

Bichko et al., "Subtype ayw variant of hepatitis B virus", FEBS Lett. 185, 208–212 (1985).

Srikumar et al., "Immunological Properties of Recombinant Porin of Haemphilus inflenzae Type b Expressed in Bacillus Subtillis", Infection and Immunity 61 (8), 3334–3341 (1993).

*Primary Examiner*—Marian C. Knode
*Assistant Examiner*—Jay F. Williams
*Attorney, Agent, or Firm*—Kathleen M. Williams; Banner & Witcoff, Ltd.

[57] ABSTRACT

The invention provides for compositions and methods for interfering with Hepatitis B viral infection that are based on the interaction of Hepatitis B virus X protein with a novel proteasome subunit.

4 Claims, 8 Drawing Sheets

FIG. 1

| FIG. 1A |
|---------|
| FIG. 1B |

```
                                                   ggagcccggcccgccggc
1    atgagctacgaccgcgccatcacgtctttctcgcccgacggcacctcttccaagtggag         60
     MetSerTyrAspArgAlaIleThrValPheSerProAspGlyHisLeuPheGlnValGlu 61   tacgcgcaggaggccgtcaagaagggctcgaccgcggttggtgttcgaggaagagacatt        120
     TyrAlaGlnGluAlaValLysLysGlySerThrAlaValGlyValArgGlyLysGluAspIle 121  gttgttcttggtgtggagaagaagtcagtggccaaactgcaggatgaaagaacagtgcgg        180
     ValValLeuGlyValGluLysLysSerValAlaLysLeuGlnAspGluArgThrValArg 181  aagatctgtgctttggatgacaacgtctctgcaggcctttgcaggcctcaccgccgatgca        240
     LysIleCysAlaLeuAspAspAsnValCysMetAlaGlyLeuThrAlaAspAla 241  aggatagtcatcaacaggccccgggagtgccagagagcccgctgactgtagaggac         300
     ArgIleValIleAsnArgAlaArgValGluCysGlnSerHisArgLeuThrValGluAsp 301  ccggtcactgtggagtacatcaccgctacatcgcaagtctgaagacagcgttatacgcag        360
     ProValThrValGluTyrIleThrArgTyrIleAlaSerLeuLysArgTyrThrGln 361  agcaatgggcgcaggccgtttggcatctctgccctcatcgtgggtttcgactttgatggc        420
     SerAsnGlyArgArgProPheGlyIleSerAlaLeuIleValGlyPheAspPheAspGly
```

FIG. 1A

```
421  actcctaggctctatcagactgaccctcgggcacataccatgcctgaaggccaatgcc  480
     ThrProArgLeuTyrGlnThrAspProSerGlyThrTyrHisAlaTrpLysAlaAsnAla 481  ataggccggggtgccaagtcagtgcgcgagttcctggagagaactatactgacgaagcc  540
     IleGlyArgGlyAlaLysSerValArgGluPheLeuGluLysAsnTyrThrAspGluAla 541  attgaaacagatgatctgaccattaagctggtgatcaaggcactcctggaagtggttcag  600
     IleGluThrAspAspLeuThrIleLysLeuValIleLysAlaLeuLeuGluValValGln 601  tcaggtggcaaaaacattgaacttgctgtcatgaggcgagatcaatccctcaagatttta  660
     SerGlyGlyLysAsnIleGluLeuAlaValMetArgArgAspGlnSerLeuLysIleLeu 661  aatcctgaagaaattgagaagtatgttgctgaaattgaaagaagaaagaaagaaacgaa  720
     AsnProGluGluIleGluLysTyrValAlaGluIleGluLysGluLysGluGluAsnGlu 721  aagaagaaacaaaagaaagcatgatgaataaaatgtctttgcttgtaattttttaaatt  780
     LysLysLysGlnLysLysAlaSerEndEnd 781  catatcaatcatgatgagtctcgatgtgtaggcctttccattccatttattcacactgag  840

841  tgtcctacaataaacttccgtattttt (poly a)
```

FIG. 1B

```
aa #             60              70
HBV   ...GLPVCAFSSAGPCALRFTSA.................
WHV   ...RLPACLASGSGPCCLVFTCA.................
             S    AAS aa #            120             130             140
HBV   ...YFKDCLFKDWEELGEEIRLKVFVLGGCRHKLVCSPAP....
WHV   ...YIKDQLLTKWEEGSIDPRLSIFLLGGCRHKCMRLL*
             R                    Y    VSQD
```

FIG. 4

COMPOSITIONS AND METHODS FOR INTERFERING WTIH HEPATITIS B VIRUS INFECTION

This invention was made in the course of work under a grant or award from the U.S. government, and therefore the U.S. government has rights in the invention.

BACKGROUND OF THE INVENTION

Hepatitis B virus (HBV) infection leads to a wide spectrum of liver injury varying from acute self-limited infection, fulminant hepatitis, asymptomatic healthy carrier state, to chronic hepatitis with progression to cirrhosis and liver failure. Moreover, chronic HBV infection has been linked to the subsequent development of hepatocellular carcinoma, a major cause of death from cancer worldwide. The pathogenesis of liver injury due to acute and chronic HBV infection is not well understood at present. The virus does not exert a cytopathic effect on hepatocytes; hepatotoxicity is likely a sequela of host immune responses to HBV antigens. In addition to hepatotropism, HBV infection has been associated with many other systemic immunological diseases such as polyarteritis nodosa, serum sickness-like syndrome, glomerulonephritis, and aplastic anemia. Therefore, the host immune responses to HBV-related antigens plays a major role in the pathogenesis of disease associated with HBV infection.

HBV is a partially double-stranded circular genome enclosed in a core structure surrounded by a lipid bilayer envelope containing Hepatitis B surface protein. HBV has a unique fourth open reading frame coding for a 16 kDa protein known as HBX. HBX appears to possess multiple functions. It activates a variety of viral and cellular promoters in diverse cell types (Colgrove et al., J. Virol. 63:4109–4026, 1989; Seto et al., Nature 344:72–74, 1990; Maguire et al., Science 252:842–844, 1991; Cross et al., Proc. Natl. Acad. Sci. USA 90:8078–8082, 1993), and therefore is a transactivator. Although the X protein does not bind to DNA directly, it activates transcription when it is targeted to a promoter by fusion to a heterologous DNA binding domain (Seto et al., supra; Maguire et al., supra; Cross et al., supra; Unger et al., The Eur. Mol. Biol. Org. J. 9:1889–1895, 1990). The protein has also been shown to function through AP-1 and AP-2 (Seto et al., supra) and to interact directly with members of CREB/ATF transcription factor family (Maguire et al., supra). Furthermore, a "Kunitz domain," characteristic of kunitz-type serine protease inhibitors, is present in HBX, and mutation of this consensus sequence inactivates the transactivation function of HBX (Takada et al., Jpn. J. Cancer Res. 81:1191–1194, 1990). In a transgenic mouse model, HBX has been shown to induce development of hepatocellular carcinoma (Kim et al., Nature 315:317–320, 1991). HBX also has been shown to play an essential role in HBV infection in vivo (Chen et al., J. Virol. 67:1218–1226, 1993; Zoulim et al., J. Virol. 68:2026–2030, 1994).

Eucaryotic cells contain multiple proteolytic systems, including the lysosomal proteases, calpains, the ATP-ubiquitin-proteasome-dependent pathway, and an ATP-independent nonlysosomal process. The major neutral proteolytic activity in the cytosol and nucleus is the proteasome, a 20S (700 kDa) particle with multiple peptidase activities. The function of the proteasome in vivo is not fully understood. However, the processing of protein antigens is believed to be accomplished by proteins of the proteasome complex. That is, small peptides are generated via proteolysis of large antigens, and are presented in the context of multiple histocompatibility complex (MHC) molecules to T lymphocytes to initiate an immune response.

One object of the invention is the identification and characterization of cellular targets of HBX.

Another object of the invention is to provide a novel cellular protein target of HBX.

Yet another object of the invention is to provide compounds that interfere with Hepatitis B virus infection by preventing productive interaction between HBX and a cellular protein target.

SUMMARY OF THE INVENTION

In one aspect, the invention features an isolated polypeptide that prevents interaction of Hepatitis B virus X (HBX) protein and XAPC7 protein. As used herein, "interaction" refers to the binding of HBX and XAPC7 to form a complex and/or to XAPC7-dependent transactivation of a viral or cellular promoter by HBX; thus, "prevents interaction" refers to the ability to disrupt binding and/or transactivation. An "isolated" polypeptide refers to a recombinant polypeptide, a chemically synthesized polypeptide, or to a highly purified (i.e., greater than 90% by weight in a mixture of polypeptides) polypeptide.

In preferred embodiments, the polypeptide may be selected from those amino acid sequences that are based on the interacting regions of HBX and XAPC7. That is, the claimed polypeptide will be encompassed by an amino acid sequence of Hepatitis B virus X protein that interacts with XAPC7, or an amino acid sequence encompassed by an amino acid sequence of XAPC7 protein that interacts with Hepatitis B virus X protein. A polypeptide of the invention will be at least 5 amino acids in length within the encompassing sequence parameters, and may be any length within the encompassing sequence sufficient to prevent interaction of HBX and XAPC7, e.g., 7 amino acids, 10 amino acids, 15, 20, 40, 50, 100 amino acids, etc. Preferably, the polypeptide prevents binding between HBX and XAPC7. As used herein, "encompassed by" is interpreted with reference to stated amino and carboxy terminal parameters and refers to a reference sequence that contains the claimed amino acid sequence in its entirety, and also includes an amino acid sequence that is identical to the stated reference sequence.

In other preferred embodiments, the isolated polypeptide comprises an amino acid sequence encompassed by amino acids 220–248 of XAPC7 presented in FIG. 1; an amino acid sequence encompassed by amino acids 198–248 of XAPC7 presented in FIG. 1; an amino acid sequence encompassed by amino acids 155–248 of XAPC7 presented in FIG. 1; and an amino acid sequence encompassed by the XAPC7 amino acid sequence presented in FIG. 1.

The invention also includes an isolated polypeptide comprising an amino acid sequence encompassed by amino acids 132–145 of Hepatitis B virus X protein presented in FIG. 4.

Preferably, the polypeptide comprises an amino acid sequence encompassed by the amino acid sequence of Hepatitis B virus X protein presented in FIG. 4.

The invention also includes an isolated polypeptide selected from the group consisting of: amino acids 198–248 presented in FIG. 1; amino acids 155–248 presented in FIG. 1; the amino acid sequence presented in FIG. 1; amino acids 132–145 presented in FIG. 4; and the amino acid sequence presented in FIG. 4.

Polypeptides of the invention are useful for interfering with Hepatitis B infection, when administered as taught herein, and are also useful as antigens to generate polyclonal or monoclonal antibodies specific for HBX or XAPC7. These antibodies may be used as a diagnostic to detect the HBX/XAPC7 complex in cells from an infected mammal as indicative of Hepatitis B growth and propagation, or to detect the individual proteins or the complex on a polyacrylamide gel, e.g., in a Western blot. Detection of the complex is critical in view of the proposed interference by HBX with proteasome function in antigen presentation.

The invention also features a recombinant nucleic acid comprising a nucleotide sequence encoding any one of the isolated polypeptides disclosed herein.

Preferably, the recombinant nucleic acid comprises the nucleotide sequence shown in FIG. 1.

Nucleic acids of the invention are useful for producing polypeptides of the invention, or as probes for detecting HBX mRNA or DNA as indicative of viral infection, or as probes for detecting XAPC7 mRNA as indicative of expression of the gene. Alternatively, the nucleic acids may be used as primers for DNA amplification of a selected segment of HBX or XAPC7 DNA.

The invention also features a host cell containing a recombinant nucleic acid as described above.

The invention also features a method of interfering with Hepatitis B virus infection in a mammal, comprising administering to a mammal suspected of harboring Hepatitis B virus a therapeutically effective amount of an isolated polypeptide, as described above. As used herein, "mammal" refers to any animal that is susceptible to Hepatitis B virus, and includes both non-primates and primates; "therapeutically effective" refers to an amount of polypeptide that results in reduction of detectable virus or virus-specific antibodies in the mammal's serum, or that results in reduction in symptoms associated with Hepatitis B virus infection. As used herein, "interfere" with HBV infection refers to significantly reducing (i.e., by 50% or more) the production of new HBV virions, as measured intra-cellularly or in serum, or to significantly reducing the titer of HBV-specific antibodies in serum, or to preventing growth of the virus, i.e., preventing replication of the viral genome. As used herein, "hepatitis B virus" refers to a family of viruses called hepadnaviruses, the family including but not limited to human HBV, woodchuck HBV, ground squirrel HBV, tree squirrel HBV, duck HBV, and heron HBV.

The invention also features a method of screening for a polypeptide that interferes with interaction of Hepatitis B virus X protein and proteasome XAPC7 protein, comprising providing Hepatitis B virus X protein, proteasome XAPC7 protein, and a candidate polypeptide suspected of inhibiting interaction of X protein and XAPC7 protein; and combining the proteins under conditions sufficient to allow for interaction of X protein and XAPC7 protein to form a complex, wherein the failure of X and XAPC7 proteins to form a complex in the presence of the candidate polypeptide is indicative of inhibition of the X/XAPC7 interaction by the candidate polypeptide.

In preferred embodiments of this method, the steps may involve in vitro or in vivo methods of providing and combining the X and XAPC7 proteins and the candidate polypeptide. For example, the proteins and candidate polypeptide may be provided and combined in vitro using synthesized or recombinant versions as described herein. Binding may be assessed using a labeled X or XAPC7 protein and conventional protein analysis, e.g., polyacrylamide gel separation followed by autoradiography. Alternatively, the X and XAPC7 proteins and the polypeptide may be provided in vivo using recombinant DNA encoding the proteins and the polypeptide and a host cell that allows for expression of the amino acid sequences. Binding and/or transactivation may be assessed as described herein, e.g., using a two-hybrid yeast system or an animal host, using conventional protein detection techniques.

Preferably, the candidate polypeptide comprises an amino acid sequence encompassed by the XAPC7 carboxy terminal amino acids 198–248 presented in FIG. 1; an amino acid sequence encompassed by the XAPC7 carboxy terminal amino acids 155–248 presented in FIG. 1; an amino acid sequence encompassed by the XAPC7 amino acid sequence presented in FIG. 1; an amino acid sequence encompassed by the Hepatitis B virus X protein amino acids 132–145 presented in FIG. 4; and an amino acid sequence encompassed by the Hepatitis B virus X protein amino acid sequence presented in FIG. 4.

The invention also includes a kit for interfering with Hepatitis B virus infection, the kit containing any one of the polypeptides described above that interferes with HBX/XAPC7 interaction, and container means therefore. The kit may further include written instructions to the effect that the polypeptide is to be administered to a mammal suspected of or known to harbor the Hepatitis B virus, preferably in a dosage that is effective to interfere with the life-cycle of the virus.

The invention also includes a kit for screening for compounds that interfere with interaction between HBX and XAPC7, the kit containing the XAPC7 protein and container means therefore. The kit may further include the HBX protein. Preferably, one or both of the XAPC7 and HBX proteins are labeled; if both proteins are labeled, then they will be differentially labeled.

Other features and advantages of the invention will be apparent from the following description of the preferred embodiments thereof, and from the claims.

DETAILED DESCRIPTION

Before describing the invention in detail, the drawings will be briefly described.

BRIEF DESCRIPTION OF DRAWINGS

FIG. 1 is the nucleotide sequence of the full-length cDNA of XAPC7 (SEQ ID NO: 1), along with the predicted amino acid sequence of the encoded protein (SEQ ID NO: 2).

FIG. 4 presents a partial amino acid sequence of HBVX (top line) and WHVX (second line) in the putative Kunitz Domains (underlined) and the residues where site-directed mutations were introduced (third line).

DESCRIPTION OF PREFERRED EMBODIMENTS OF THE INVENTION

Figure 2:
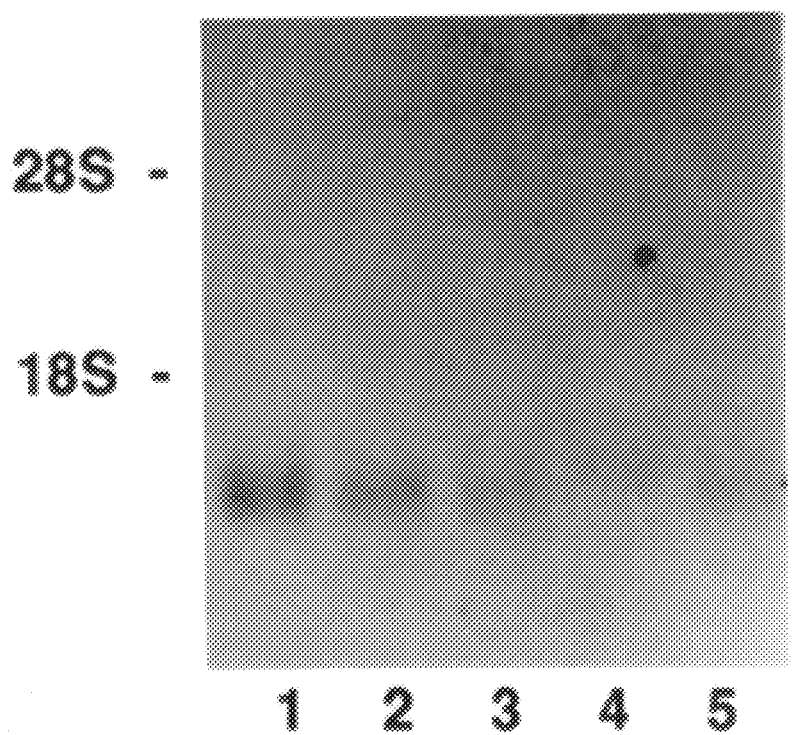
FIG. 2 is a Northern blot analysis of several human cell lines probed with an XAPC7 DNA probe.

The invention is based on discovery of interaction between Hepatitis B virus X protein and a newly isolated and characterized protein of the proteasome complex, XAPC7. The invention features polypeptides corresponding to regions of interaction between the HBX and XAPC7 proteins and whose presence results in disruption of interaction between the two proteins. Example I provides a description of the identification, cloning, and sequence determination of a cellular target of HBX, i.e., the proteasome subunit XAPC7, and provides the complete nucleotide sequence of XAPC7 and its predicted amino acid sequence. Example II provides methods of testing of interaction between HBX and other proteins of the proteasome complex. Example III provides methods for localization of the region of the Hepatitis B virus X protein that interacts with the XAPC7 molecule using HBX mutants. Example IV provides methods of testing candidate polypeptides that interfere with the interaction of HBX and XAPC7, and thus interfere with the HBV life-cycle. Example V provides methods for making polypeptides of the invention. Example VI provides results of in vivo testing of candidate polypeptides for interference with HBX and XAPC7 interaction. Example VII provides for methods of making nucleic acids encoding polypeptides of the invention and antibodies specific for such polypeptides.

EXAMPLE I

A proteasome subunit has been identified and characterized that interacts specifically with HBX, and therefore appears to be a functional target of HBX in vivo. This proteasome subunit, XAPC7, was identified and characterized as follows.

HBX appears to function as a transactivator in a variety of cell types including Hela cells. Thus, a Hela cell cDNA library containing cDNAs fused to the B42 activation domain in the yeast vector JG4-5 was used to screen for clones interacting with HBX. Four independent clones were identified. One clone strongly reacted (XAPC7) and was selected for further analysis. The screening system was as follows.

The HBX gene derived from an HBV adw strain (ATCC Nos. 45020 and 67193, or Robinson, in Fields, Virology, 2d ed., Raven Press, 1990, hereby incorporated by reference) was fused to the lexA DNA binding domain (pEG202) through the Nco 1 site (nucleotide 1375), which contains the AUG start codon of HBX. Using the yeast two hybrid system (Fields et al., Nature 340:245–246, 1989 and Gyuris et al., Cell 75:791–803, 1993, hereby incorporated by reference; see also FIG. 6), two reporter constructs were used in selection of the candidate clones; one contains the lexAop-Leu2 gene which allows for cell growth in the absence of leucine, the other has the lexAop-lacZ gene which permits selection based on β-gal activity (pSH18–34). For screening and in initial experiments, the pSH18–34 lacZ reporter which contains eight LexA binding sites was used. In subsequent experiment, where the interaction is expected to be strong, such as the one between HBX and XAPC7, a less sensitive JK103 which contains two copies of LexA binding sites was used as the lacZ reporter. The cDNA library was transfected along with the X expression construct into EGY48 harboring both reporters. Thus, the EGY48 yeast strain containing the LexAop-Leu2 and JK103 reporters was transformed with (1) pEG202HBX and JG4-5, (2) pEG202HBX and JG4-5XAPC7, (3) pEG202HBXRsr and JG4-5XAPC7, (4) pEG202HBXEn and JG4-5XAPC7, (5) pEG202XAPC7 and JG4-5HBX, (6) pEG202- and JG4-5HBX, (7) pEG202- and JG4-5XAPC7, and (8) pEG202XAPC7 and JG4-5. Transformants were spotted on 4 types of plates as indicated at the left and top, and the plates were photographed 3 days later. The sample positions are identical on each plate.

A pool of cells containing 2×10$^6$ primary library transformants were plated onto galactose-Leu$^-$ selection plates. The leu$^+$ clones were patch-transferred to galactose-Leu$^-$ selection plates containing X-gal. Approximately 200 clones showed detectable blue color. They were streaked out on 4 types of plates, glu-leu$^-$, gal-leu$^-$, glu-leu$^+$-X-gal, and gal-leu$^+$-X-gal. Nine clones showed definitive galactose-inducible leucine dependence and LacZ activity. Plasmids isolated from these clones were transfected into E. coli K-12 strain KC8 which allows for selection of the Trp marker carried by the library vector JG4-5. All 9 clones have cDNA inserts ranging from 0.5 to 1.5 kbp. Cross-hybridization demonstrated that some of them were derived from the same cDNA, resulting in a total of 4 groups. These clones were re-transfected back into EGY48 with HBX and the reporter constructs and they again demonstrated galactose-inducible leucine dependence and LacZ activity. In addition, transfection of these cDNA clones with pEG202 that contains the LexA DNA binding domain only (pEG202-) did not result in any transactivation of the reporter genes, indicating that specific interaction with the HBX domain of the lexA-HBX fusion protein is required. One of the cDNA clones (XAPC7) showing strong interaction was selected for further analysis.

Two HBX mutants were generated for initial analysis. One contains an amino acid (aa) insertion of arginine after aa #68 (HBXRsr); this was constructed by digesting the HBX sequence with Rsr II and then filling in the 3 nucleotide overhang with Klenow enzyme. The other contains a C-terminally truncated HBX gene ending at aa #90 (HBXEn), which was generated by truncating the HBX gene at EcoN1 restriction site (nucleotide 1645). To switch the interaction domains, HBX was fused in frame to the B42 acid patch transactivation domain of JG4-5 and XAPC7 to the lexA DNA binding domain of pEG202.

The two HBX mutants described above, one containing amino acid insertion of arginine after aa #68 (HBXRsr) and the other being a truncated N-terminal HBX (aa #1–90) (HBXEn) were included as controls. HBXRsr appeared to interact with XAPC7 but HBXEn was totally nonreactive. To demonstrate that this particular interaction between HBX and XAPC7 is not peculiar to the fusion proteins (lexA or B42), the reverse constructs were generated—HBX fused to the B42 activation domain in JG4-5 and XAPC7 fused to the lexA DNA binding domain. The result showed that this interaction between HBX and XAPC7 is specific regardless of the backbone of the fusion protein.

The full-length cDNA of XAPC7 was subsequently obtained from a λGT11 Hela cDNA library (FIG. 1). FIG. 1 shows the complete nucleotide and predicted amino acid sequence of XAPC7, based on sequencing of the full-length XAPC7 cDNA clone isolated from a λGT11 Hela cDNA library. The initiation AUG codon was identified at the 5' end with appropriate Kozak consensus sequence. The entire ORF codes for 248 amino acids with an Mr of 27,896 kDa. Sequencing analysis of the XAPC7 clone (FIG. 1) reveals that it encodes for a polypeptide with high sequence homology to the PROS-28.1 subunit of proteasome (multicatalytic proteinase complex) of Drosophila melanogaster (Haass et al., Gene 90:235–241, 1990) and the α proteasome subunit of Arabidopsis thaliana (Genschik et al., J. FEBS Letters 309:311–315, 1992). It shows weaker but significant sequence homology to the other members of the proteasome family (Tanaka et al., The New Biologist 4:173–187, 1992). Sequence alignment between XAPC7 and its closest human relative HC8 is also shown (33% identity and 57% similarity). The fact that XAPC7 represents a highly conserved proteasome subunit with>65% amino acid identity among members of both animal and plant kingdoms, supports the functional importance of this subunit. The domain interacting with HBX resides in the C terminus of the XAPC7 protein (i.e., encompassed by amino acids 137–248). The full-length XAPC7 was also shown to interact with HBX in the yeast (data not shown).

Using the XAPC7 cDNA as hybridization probe and washing under stringent condition, Northern blot analysis of RNA from several human and mouse cell lines, and human placenta (Clonetech) was performed and revealed a 1.0 kb XAPC7 transcript (FIG. 2). In FIG. 2, lane 1, human hepatoma cell line HepG2; lane 2, human hepatoma cell line HuH-7; lane 3, COS7; lane 4, mouse lymphoma cell line EL4, lane 5, human placenta RNA. The positions of 28S and 18S are indicated. A similar-size RNA species was also identified in RNA from a mouse lymphoma cell line.

EXAMPLE II

Other subunits of the proteasome family were also tested for interaction with HBX. cDNAs of five other human proteasome subunits (LMP-2, HC2, HC3, HC5, and HC8) (Brown et al., Nature 353:355–357, 1991; Glynne et al., Nature 353:357–360, 1991; Tamura et al., Biochimica et Biophysica Acta 1089:95–102, 1991) were cloned into yeast JG4-5 vector for interaction studies in yeast.

The carboxy-terminal portion of each cDNA for LMP-2, HC2, HC3, HC5, and HC8 proteasome subunits was inserted into JG4-5 to form a fusion protein with the B42 activation domain. Using PCR, the C-terminal portions of each of LMP-2 at amino acid (aa) 117, HC2 at aa 134, HC3 at aa 136, HC5 at aa 145, and HC8 at aa 138, which corresponds in sequence homology alignment to the original XAPC7 clone (aa #137–248), were inserted into JG4-5 to form fusion proteins with the B42 activation domain. The X gene of WHV derived from WHV81 strain was fused to the lexA DNA binding domain through the Nco 1 site of WHV (nt 1501), which contains the AUG start codon of WHVX. The resulting constructs by themselves did not activate the reporter (not shown). The constructs were then tested for transactivation of the reporter construct, as described above. Sample 1 is pEG202HBX and JG4-5XAPC7; sample 2, pEG202WHVX and JG4-5XAPC7; sample 3, pEG202HBX and JG4-5LMP-2; sample 4, pEG202HBX and JG4-5HC2; sample 5, pEG202HBX and JG4-5HC3; sample 6, pEG202HBX and JG4-5HC5; sample 7, pEG202HBX and JG4-5HC8.

The results showed that no interaction was observed between HBX and the proteasome subunits tested other than XAPC7. Since woodchuck hepatitis B virus also encodes an X protein (WHVX) with transactivation function and significant homology to HBX, WHVX was analyzed for its interaction with XAPC7 in yeast. The results showed that WHVX also interacts specifically with XAPC7. Experiments were as follows.

In order to demonstrate interaction of HBX and XAPC7 proteasome subunit in vitro, we constructed two GST-fusion expression plasmids, one with HBX and the other with the XAPC7 protein. The GST-HBX and GST-XAPC7 fusion proteins expressed in bacteria were purified with glutathione beads and then incubated with in vitro translated, [$^{35}$S]-Met labeled full-length XAPC7 and HBX polypeptides, respectively. Binding reactions with GST only were performed as controls in each binding assay.

In vitro binding experiments were performed as follows. HBX and full-length XAPC7 were cloned into pGEM11Zf (+) vector (Promega, Madison, Wis.) and their transcripts were produced using in vitro transcription kit (Promega). Rabbit reticulocytelysates from Promega were used to generate [$^{35}$S]-Met labeled proteins, which were used immediately for binding studies. HBX (full-length) and XAPC7 (aa #137–248) were cloned separately into the pGEX-KG vector (Pharmacia, Piscataway, N.J.) to be expressed as a fusion protein with the glutathione-S transferase. The binding reactions were performed in NETN buffer (0.5% of NP-40, 20 mM Tris pH 8.0, EDTA 1 mM, 100 nM NaCl) at room temperature for 1 hour with constant mixing. The beads were washed extensively with the same buffer and the bound proteins were subjected to 15% SDS-PAGE analysis.

Figure 3A:
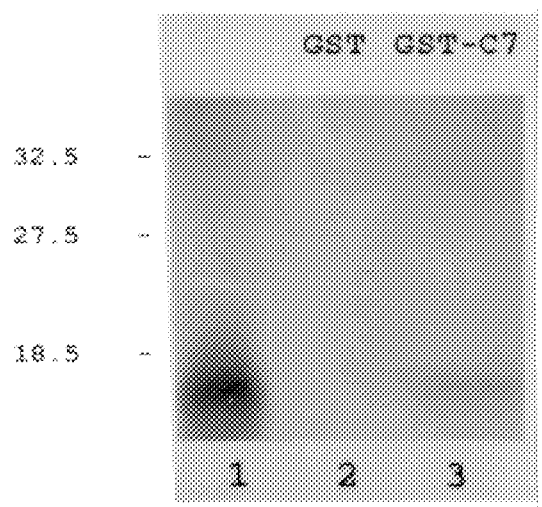
FIG. 3 is an autoradiogram of a polyacrylamide gel of HBX bound to XAPC7.
Figure 3B:
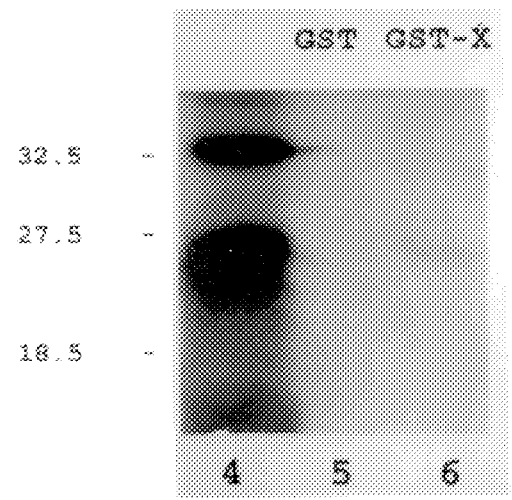

In FIG. 3, the in vitro translated protein products are shown in lane 1 as HBX and lane 4 as XAPC7. The other lanes are as indicated. The background labeling of a 35 kDa is often seen in this preparation of rabbit reticulocytelysates (Promega). This irrelevant protein product represents an internal control for binding to the GST fusion protein-containing beads.

The results, shown in FIG. 3, demonstrate that HBX bound specifically to GST-XAPC7 and not GST alone; similar binding was also seen between XAPC7 and GST-HBX.

EXAMPLE III

Structural and functional mapping of HBX have defined two domains that are crucial for the transactivation function of HBX (Takada et al., supra; Arii et al., Oncogene 7:397–403, 1992; Runkel et al., Virology 197:529–536, 1993). These two domains appear to overlap with the putative "Kunitz-type" domain of protease inhibitor that are present in both HBX and WHVX. Several key residues in these two domains were mutated and studied with respect to the transactivation function of HBX and interaction between HBX and XAPC7 in the yeast two-hybrid system. The glycine and cysteine residues were mutated in both domains (FIG. 4); several other conserved residues were also mutated. In FIG. 4, amino acid sequences of HBX and WHVX around the putative Kunitz Domains (underlined) are shown. Amino acid numbers of the HBX protein are shown at the top. Site-directed mutations (shown at the bottom of the amino acid residues) were introduced and are numbered as MT1 to 10 sequentially: MT1 with Cys to Ser mutation at aa #61, MT2 with Gly to Ala mutation at aa #67, MT3 with Pro to Ala at aa #68, MT4 with Cys to Ser at aa #69, MT5 with Trp to Arg at aa #120, MT6 with Phe to Tyr at aa #132, MT7 with Gly to Val at aa #136, MT8 with Cys to Ser at aa #137, MT9 with Arg to Gln at aa #138, MT10 with His to Asp at aa #139. An additional mutant, MT11, was generated by replacement of aa residues 137 to 141 (Cys-Arg-His-Lys-Leu) with Val-Met sequence. The HBXRsr mutant has been described previously.

To obtain a structure-function correlation of this interaction, the mutants were also tested for their transactivation activities. Since HBX has been shown to activate transcription through AP-1, AP-2, AP-3, NF-κB and SP-1 factors (Seto et al., supra; Maguire et al., supra; Kekule et al., Nature 361:742–745, 1993), the effects of these mutants were tested on five reporter constructs, each of which contains a cis-acting sequence responsive to each of the five factors. Rous Sarcoma Virus (RSVO LTR, which has been shown to be transactivated by HBX, was also tested. The results are shown in FIG. 5.

Figure 5:
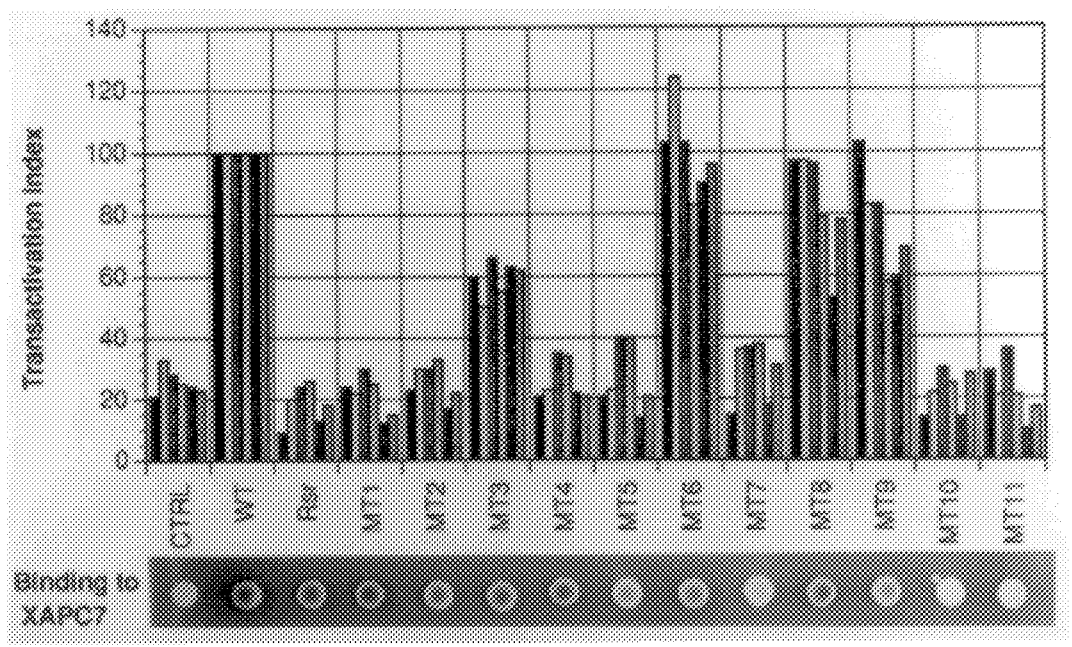
FIG. 5 shows results of transactivation and binding between XAPC7 and HBX mutants.

In FIG. 5, reporter constructs directed by AP-1, AP-2, Ap-3, NF-kB, SP-1 and RSV were co-transfected with HBX mutant expression constructs into HepG2 cells. The reporter activity of each mutant was shown as percentage of activity of wild-type HBX (indicated as transactivation index in the figure). Interactions of HBX mutants and XAPC7 are shown below the transactivation activity of each mutant. The light grey color of the MT5, suggestive of diminished binding, was consistently observed in various experiments.

HBX mutants were generated by PCR and confirmed by sequencing. Wild-type and mutant HBX genes were cloned into the pCD.1 expression vector (Invitrogen) for transactivation studies. HBX mutants were also constructed into pEG202 for interaction studies in yeast. CAT reporter constructs containing either 4 AP-1, 6 AP-2, 5 AP-3, or 3 NF-kB sites in front of a minimal human metallothionein IIA promoter (MT-IIA) were described previously (Maguire et al., supra). Another reporter construct contains 2 SP-1 sites (5' GGGCGGGGCAGGG 3') cloned into the pTK81Luc plasmid which consists of a minimal HSV TK promoter in front of the luciferase gene (Nordeen, S. K., Biotechniques 6:454–457, 1988). The reporter construct for RSV is RSV-Luc. The minimal MT-IIA and TK promoter-driven reporter constructs had low activities in transfected cells and were not transactivated by co-transfection with HBX expression construct (not shown). Calcium phosphate co-transfection of HBX expression constructs and reporter plasmids were performed at a ratio of 1 to 5 with a total DNA of 0.3 μg per well in 6-well plate. Reporter activities were assayed two days later. Data presented are the mean values of transfections done in triplicate and the results are representative of three separate experiments.

The mutations tested here appeared to affect the transactivation of all the reporters equally, suggesting that HBX exerts its transactivation function through a single functional pathway. This observation was also corroborated by transfection studies in CV-1 cells (data not shown). The glycine (MT7) and histidine (MT10) mutations in the second domain eliminated both the transactivation and binding properties. The cystein mutation (MT8) did not affect the binding or transactivation. MT11 with a partial deletion of the second domain also had no activities in both transactivation and binding. Other conserved residues in the second domain, such as phenylalanine (MT6) and arginine (MT9), appeared not to be essential for XAPC7 binding or function of HBX. Mutagenesis analysis in the second domain of HBX shown in FIG. 4 demonstrated a close association between the ability of the mutants to interact with XAPC7 and the transactivation activity of the mutants.

Mutagenesis studies of the first domain of HBX (shown in FIG. 5) demonstrated that this domain is not important for interaction with XAPC7 but is critical for HBX transactivation function. The glycine (MT2) and two cysteine (MT1 and 4) mutations in the first domain appeared to abrogate the transactivation function of HBX without affecting the binding to XAPC7. The mutant with proline to alanine substitution (MT3) in the first domain seemed to retain 50–60% of the transactivation activities of wild-type HBX but bound to XAPC7 as WT HBX did. These data are consistent with the phenotype of the HBXRsr and HBXEn mutants described previously. This observation suggests that HBX may interact with another cellular factor through the first domain and this interaction is equally critical for the function of HBX. The two cysteine residues in the first domain might be important in the formation of disulfide bond. Finally, because of the highly conserved tryptophan residue at aa #120, an additional mutation was introduced at this position (MT5, Trp to Arg). Transactivation and interaction analyses showed that this HBX mutant does not transactivate but retains part of the binding activity to XAPC7. This conserved tryptophan residue, therefore, may contribute to the binding of the second domain of HBX to XAPC7.

EXAMPLE IV

The invention also encompasses a method of screening for compounds that interfere with binding of HBX protein to the XAPC7 proteasome subunit. Thus, a candidate polypeptide according to the invention may be tested for ability to interfere with interaction between HBX and XAPC7, as follows.

An in vitro screening method for candidate polypeptides that interact with HBX or XAPC7 is as follows. This system is described above with respect to demonstrating HBX/XAPC7 interaction.

Two glutathione-S transferase (GST)-fusion expression plasmids are generated as described above, one encoding a GST-HBX fusion protein, the other encoding a GST-XAPC7 fusion protein. These proteins are generated in a rabbit reticulocytelysate system using RNAs transcribed in vitro from the genes, or are generated in bacteria as fusion proteins which are purified with glutathione beads, as described above, Binding reactions include an $^{35}$S-Met labeled GST-fusion protein and a candidate polypeptide fusion protein in NETN buffer (see above). Binding reactions with GST only are performed as controls in each binding assay. The beads are then washed and bound proteins are analyzed on SDS-PAGE. The labeled GST-fusion protein is used above to determine the control migration position. Binding of a candidate polypeptide is determined by comparison of migration of the candidate polypeptide with respect to the unbound labeled protein. That is, if a larger protein complex is apparent on the gel in the appropriate sample lane, then this indicates binding of the candidate polypeptide to the labeled fusion protein. Failure of the candidate polypeptide to bind is indicated by migration of the sample protein mixture to the control label position.

Figure 6:
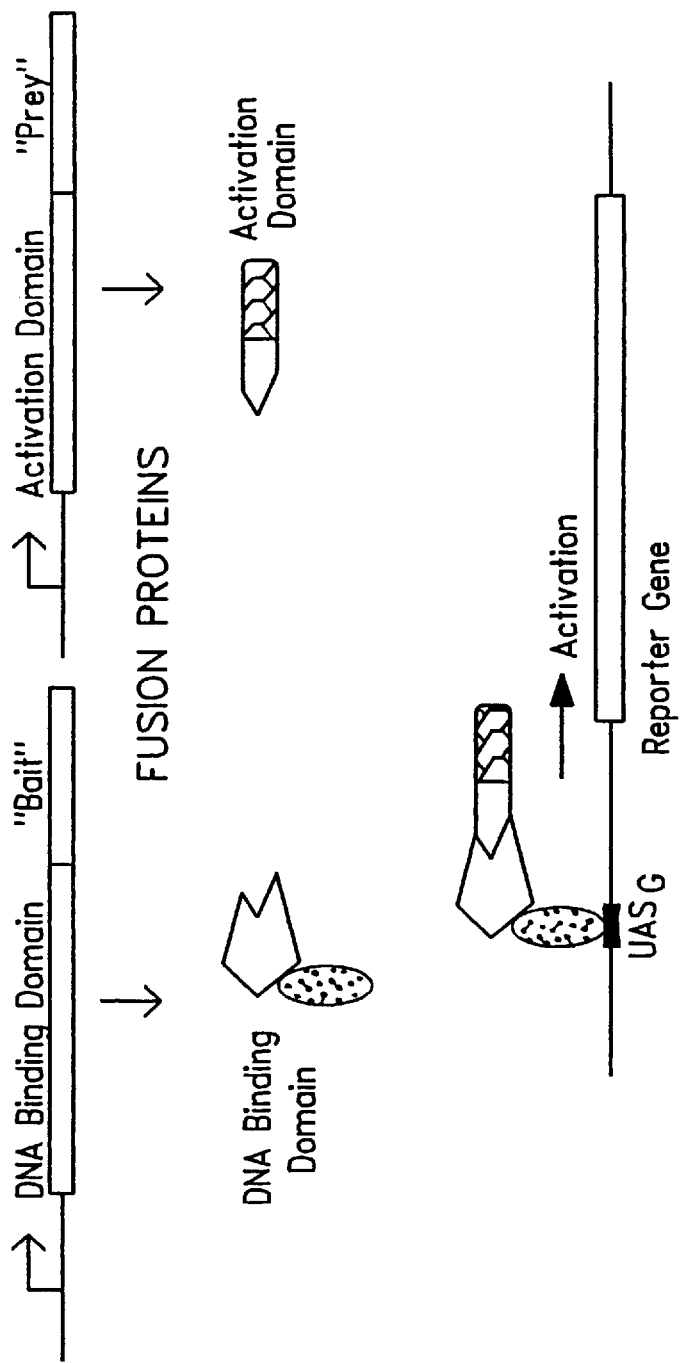
FIG. 6 is a schematic illustration of a transactivation system for testing candidate compounds of the invention.

An in vivo method of screening candidate compounds according to the invention for interaction with the HBX or XAPC7 proteins is as follows. FIG. 6 schematically illustrates the yeast two hybrid system. This system is described above for identification of the XAPC7 protein as a cellular factor that interacts with HBX. The system is also described above for identification of HBX mutants that fail to transactivate the reporter gene when combined in the system with XAPC7. As shown above, some of these mutants may, however, retain the ability to bind to XAPC7.

Other compounds, e.g., polypeptides, may be tested for transactivation and binding using this system, which is briefly described below.

With reference to FIG. 6, in brief, two different DNA constructs capable of replicating in yeast are prepared. The first construct includes a gene coding for a protein or polypeptide to be tested fused to a gene encoding a known DNA-binding polypeptide that does not activate transcription by itself, for example, the DNA binding domain of GAL4 (amino acids 1–147) or LexA (amino acids 1–202). The second construct includes a gene coding for an activation domain, i.e., a transcriptional activator, such as that of GAL4 (amino acids 768–881), fused to one of HBX or XAPC7 to provide a binding domain. Thus, if the candidate polypeptide comprises an amino acid sequence from the HBX protein, the first construct is a fusion protein of GAL4 (amino acids 1–147) and the candidate HBX polypeptide, and the second construct will encode a fusion protein of GAL4(768–881) and XAPC7 (or a domain fragment thereof that binds to HBX). Alternatively, if the candidate polypeptide comprises an amino acid sequence from the XAPC7 protein, the first construct is a fusion protein of GAL4 (amino acids 1–147) and the candidate XAPC7 polypeptide, and the second construct will encode a fusion protein of GAL4 (768–881) and HBX (or a domain thereof that binds to XAPC7). The second construct by itself does not activate transcription because it contains no DNA binding domain (that is, it contains only a binding domain specific for the HBX/XAPC7 interaction). The reporter construct contains the cognate DNA binding sequence of the DNA binding domain upstream of a gene that produces a protein with enzymatic activity, such as β-galactosidase, or an auxotrophic marker, such as Leu-2, which is required for leucine synthesis. The interaction of two proteins will bring the DNA binding and activation domains, e.g., of GAL4, together to activate transcription of the reporter gene, thus enabling identification of a yeast clone containing the candidate polypeptide that interacts with the HBX or XAPC7 protein.

In addition, in another alternative assay similar to the two hybrid system described above, the first and second constructs may include HBX and XAPC7 fusion proteins, as described in the above Examples. A third construct may be provided to the cell which encodes and allows for expression of a candidate polypeptide. Thus, if the expressed candidate polypeptide interferes with interaction between the HBX and XAPC7 fusion proteins, the reporter gene will not be expressed. In contrast, absent an interfering candidate polypeptide, the HBX and XAPC7 interaction will occur and the reporter gene will be expressed.

Preparation of DNA constructs, yeast transformation, and identification of transactivating or non-transactivating clones are described in detail above for identification of the XAPC7 cellular proteasome subunit and in Fields et al., 1989, supra, and Gyuris et al., 1993, supra). Appropriate modifications of the system to accomplish substitution of DNA encoding a candidate polypeptide rather than a complete protein will be readily apparent to one of skill in the art.

Polypeptides of the invention may also be tested in a suitable animal model. Polypeptides that are able to interfere with the Hepatitis B virus X protein/XAPC7 interaction may be tested in the woodchuck system, as described in detail in Chen et al., Jour. Virol. 67;1218 (1993) and Zoulim et al., Jour. Virol. 68;2026 (1994), both of which are hereby incorporated by reference.

Polypeptides that are found to interfere with the HBX/XAPC7 interaction via any one of the in vitro or in vivo tests described above may be of further use in stimulating the immune response to HBV infection. That is, without being bound to any one theory, it is proposed that the binding of HBX to XAPC7 of the proteasome interferes with proteasome function, thus preventing viral antigen presentation in HBV-infected cells.

EXAMPLE V

Proteins and polypeptides of the present invention will have sequences as described herein and may be produced by de novo synthesis, or by expression of a suitable nucleic acid in a suitable expression system in vitro or in transfected cells, or they may be obtained by extraction from natural sources in which case the proteins will be substantially pure and free from other protein and non-protein material with which they are naturally associated in vivo.

The polypeptides and proteins of the invention may be used for treatment of HBV infection in a mammal or for generating antibodies.

In a particular aspect, the invention relates to polypeptides having a sequence of at least 5 contiguous amino acid residues corresponding to a sequence of the same length as presented in FIGS. 1 to 4 or alleles thereof. Polypeptides will preferably be 7 or even 10, 20, 50, 100 or 200 or more residues in length. Those longer than 5 residues may differ in one or more residues from the sequence presented in FIGS. 1 to 4. Differences may be by substitution deletion or insertion. Polypeptides preferably have at least 75%, more preferably 85%, 90% or even 99% homology with the relevant portion of the sequence presented in FIGS. 1 to 4 or alleles thereof.

In another aspect, the invention relates to proteins and polypeptides which contain epitopes corresponding to one or more epitopes of the XAPC7 protein, or mimetopes thereof, or which are capable of interrupting association of HBX and XAPC7, or which are capable of interrupting association of HBX and XAPC7 so as to prevent proteolysis of the proteasome by specific reversible or irreversible binding. Such proteins and polypeptides may be identified by appropriate assay techniques, for instance as described herein.

Antibodies may be whole antibodies such as IgM or, preferably IgG; they may be polyclonal or monoclonal. The term "antibody" includes fragments of antibodies containing the antigen-recognition site such as F(ab) and $F(ab^1)_2$ fragments, single domain antibodies (DABs), complementarity-determining regions (CDRs) and minimal recognition units (MRUs). The term "antibody" further includes anti-idiotypic antibodies and anti-idiotype-2 antibodies (i.e. antibodies against anti-idiotype-2 antibodies) and fragments,DABs, CDRs, and MRUs thereof. Anti-idiotypic antibodies are those which recognize the antigen-recognition site of an antibody. Anti-idiotypic antibodies therefore mimic the antigen whereas anti-idiotype-2 antibodies mimic the antibody.

Antibodies may be obtained by conventional immunization techniques and extracted from the body fluids of immunized animals. Alternatively, they may be obtained by culturing antibody secreting cells obtained from such immunized animals, preferably after immortalization by fusion with myeloma cells and other well known techniques. In another alternative, antibodies may be obtained by expressing genetic material, obtained from such antibody secreting cells, in transfected cells.

Antibodies specific for polypeptides or proteins of the present invention are useful in detection of HBX or XAPC7 proteins used in the screening methods described herein, or for preventing association of HBX and XAPC7, and thus for interfering with the HBV life-cycle or for preventing proteolysis by the proteasome.

Cells which secrete antibodies may be obtained by conventional techniques and include antibody-secreting cells obtained from animals immunized against an appropriate antigen, antibody-secreting cells obtained from immunized animals and immortalized by fusion with myeloma cells to form hybridomas, by use of Epstein Barr virus and other known immortalizing techniques and cells capable of expressing and, preferably, processing antibodies on the basis of exogenous nucleic acid inserts.

Antibodies specific for polypeptides of the invention have a variety of uses, including interfering with HBX/XAPC7 interaction, identification of the cognate epitope (protein) in the cell, or for identification of the cognate antigen or the HBX/XAPC7 complex via polyacrylamide gel electrophoresis or Western blotting (see Maniatis et al., 1990, Molecular Cloning, A Laboratory Manual, Cold Spring Harbor Press, CSH, N.Y., hereby incorporated as reference).

EXAMPLE VI

Polypeptides corresponding to portions of the XAPC7 carboxy terminus, i.e., the region encompassing amino acids 137–248, were tested for the ability to interfere with the HBX/XAPC7 interaction or to bind to HBX, as follows.

Figure 7:
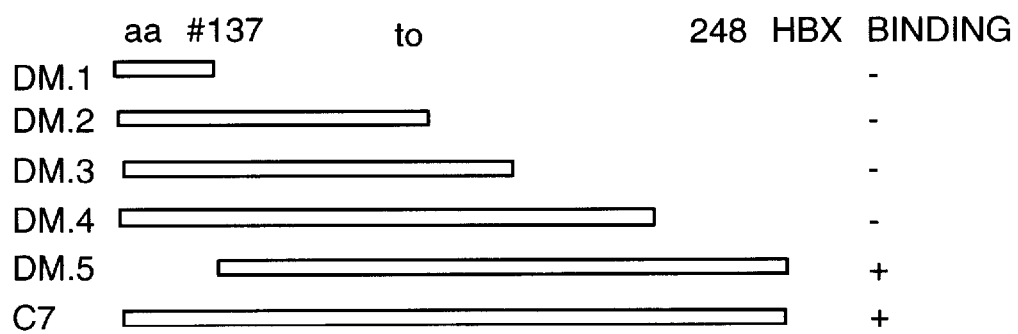
FIG. 7 is a schematic illustration of various polypeptides of the invention and results of binding experiments.

XAPC7 polypeptide fragments were tested for binding to HBX, as follows. Deletion constructs of XAPC7 polypeptide-encoding DNA were generated and tested for binding to HBX in yeast cells. Deletion mutants were generated using convenient restriction sites. These mutants are DM.1 (containing amino acids 137–155; DM.2 (containing amino acids 137–188); DM.3 (containing amino acids 137–198); DM.4 (containing amino acids 137–220); DM.5 (containing amino acids 155–248). The deletion mutants were cloned into JG4-5 and analyzed for interaction with pEG202HBX in yeast, as described above. The results, shown in FIG. 7, reveal that the 90 amino acid polypeptide corresponding to the XAPC7 carboxy terminal region between and including amino acids 155 and 248 is effective in binding to HBX. Comparison of the DM.4 and DM.5 results suggests that the region encompassing amino acids 220–248 is critical for binding to HBX. Additional data using a XAPC7 deletion mutant containing carboxy terminal amino acids 198–248 demonstrates that this 50 amino acid polypeptide binds to HBX.

EXAMPLE VII

Except as otherwise required, nucleic acids of the invention may be DNA or RNA. The nucleic acids may be single stranded or double stranded. Double stranded nucleic acids may be blunt ended or have 5' or 3' extensions at one or both ends; they may contain one or more restriction endonuclease recognition and/or cutting sites and one or both ends may be cut ends obtained by restriction endonuclease cutting or designed for ligation. Single stranded DNA may be a template strand or a complementary (non-template) strand. DNA may be cDNA, genomic DNA or synthetic DNA. RNA may be mRNA, sense or antisense RNA.

Nucleic acids of the invention may be produced by de novo synthesis and, if necessary, by assembly of fragments to create longer sequences, or obtained from natural sources such as from human cells or by cloning or amplification of natural or synthetic nucleic acids including by transcription or reverse transcription in vitro or in host cells.

Nucleic acids of the invention are useful in diagnosis for instance as hybridization probes for following alleles of HBX or XAPC7 genes through family trees to identify at risk individuals where particular alleles are associated with particular diseases, or to identify mutated or damaged genes in an individual. These nucleic acids are also useful as probes for HBV productive infection, or as primers for amplification of a selected region of HBX or XAPC7 DNA.

In a particular aspect, the invention relates to nucleic acids having a sequence of at least 17 contiguous nucleotide bases or base pairs corresponding to a sequence of the same length within the sequence set out in FIGS. 1 and 4 or alleles thereof. Preferably the nucleic acid contains at least 20, more preferably 50, 100 or even 200 or more bases or base pairs in a sequence corresponding to that of FIGS. 1 and 4. Nucleic acid of a total of 17 bases or base pairs will have a sequence identical to the relevant portion of the sequences of FIGS. 1 and 4 or alleles thereof or will be exactly complementary thereto. Nucleic acids longer than 17 bases or base pairs may have a sequence exactly the same as or differing from the relevant portion of the sequence of FIGS. 1 and 4 or alleles thereof in one or more bases or base pairs or complementary to such a sequence. Differences may be by substitution, deletion or insertion but should not preserve the reading frame where the nucleic acid is intended to be expressed. Preferably such nucleic acids have at least 75%, more preferably 85%, 90% or even 99% homology with the relevant portion of the sequence of FIGS. 1 and 4 or alleles thereof.

In another aspect, the invention relates to nucleic acids encoding proteins or polypeptides of the invention by use of alternative codons to those used in the normal HBX and XAPC7 genes.

Cloning vectors, expression vectors, viral genomes (and virus particles containing such genomes), transfected prokaryotic and eukaryotic cells and transgenic animals of the invention all contain exogenous nucleic acids of the invention and may be produced by conventional techniques.

These vectors and expression systems may variously be used for amplification of nucleic acids of the invention, as diagnostic reagents or therapeutic agents and as sources of materials such as nucleic acids, proteins or polypeptides and antibodies which are themselves products of the invention.

For in vitro and in vivo procedures and for other reasons well known to those skilled in the art, it is often convenient to provide products such as the nucleic acids, proteins, peptides and antibodies of the invention with detectable labels. Such labels, for instance radio isotopes, fluorescent chromophores, enzymes, metal particles and polyester beads may be bonded to the products of the invention, used and detected by conventional techniques. Labeled products form a particular aspect of the invention.

For therapeutic applications and in vivo diagnostic procedures and for other reasons well known in the art, it is often useful to target HBX to a particular site using the recognition properties of a targeting entity such as an antibody.

Diagnostic and screening methods of the invention include all conventional techniques practiced in vitro including nucleic acid hybridizations and immunoassays based on the use of antibodies or proteins or polypeptides of the invention including direct or competitive protein/protein binding assays, ELISA, RIA and fluorescent assays.

USE

The invention provides compositions and methods used for treatment of Hepatitis B viral infection in mammals when administered as described herein. The compound is preferably administered via oral, intravenous or parenteral modes. A therapeutically effective amount of a polypeptide composition of the invention will be in the range of about 0.1 mg–50 mg/kg body weight/day; preferably in the range of 5–20 mg/kg/day. The compound may be administered with a pharmaceutically acceptable carrier substance, e.g., magnesium carbonate, lactose, or a phospholipid with which the compound can forma micelle, together can form a therapeutic composition, e.g., a pill, tablet, capsule or liquid for oral administration to the mammal. Other forms of compositions are also envisioned, e.g., a liquid capable of being administered nasally as drops or spray, or a liquid capable of intravenous, parenteral, subcutaneous, or intraperitoneal administration. The compound may be in the form of a biodegradable sustained release formulation for intramuscular administration. For maximum efficacy, zero order release is desirable, e.g., using an implantable or external pump, e.g., an Infusaid™ pump (Infusaid Corp, Mass.).

OTHER EMBODIMENTS

The invention may be embodied in other specific forms without departing from the spirit and scope thereof. Accordingly, other embodiments are within the following claims.

We claim:

1. A polypeptide consisting of the amino acid sequence GLPVCAFSSAGPCALRFISA (SEQ ID NO:3).

2. A polypeptide consisting of the amino acid sequence YFKDCLFKDWEELGEEIRLKVFVLGGCRHKLVCSPAP (SEQ ID NO:5).

3. A polypeptide consisting of the amino acid sequence FVLGGCRHKLVCSP (positions 22–35 of SEQ ID NO:5).

4. A method of screening for a polypeptide that interferes with interaction of Hepatitis B virus X protein and proteasome subunit XAPC7 protein, comprising providing Hepatitis B virus X protein, proteasome XAPC7 protein, and a candidate polypeptide suspected of interfering with interaction of said X protein and said XAPC7 protein;

combining said proteins under conditions sufficient to allow for interaction of said X protein and said XAPC7 protein to form a complex; and detecting said complex, wherein the failure of said X and said XAPC7 proteins to form a complex in the presence of said candidate polypeptide is indicative of interference with said interaction by said candidate polypeptide.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 890 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 22..750

( x i ) SEQUENCE DESCRIPTION: SEQ ID NO:1:

```
GGAGCCCGGC  CGCCCGCCGG  C  ATG  AGC  TAC  GAC  CGC  GCC  ATC  ACC  GTC  TTC         51
                           Met  Ser  Tyr  Asp  Arg  Ala  Ile  Thr  Val  Phe
                            1                    5                        10

TCG  CCC  GAC  GGC  CAC  CTC  TTC  CAA  GTG  GAG  TAC  GCG  CAG  GAG  GCC  GTC      99
Ser  Pro  Asp  Gly  His  Leu  Phe  Gln  Val  Glu  Tyr  Ala  Gln  Glu  Ala  Val
                    15                  20                       25

AAG  AAG  GGC  TCG  ACC  GCG  GTT  GGT  GTT  CGA  GGA  AGA  GAC  ATT  GTT  GTT    147
Lys  Lys  Gly  Ser  Thr  Ala  Val  Gly  Val  Arg  Gly  Arg  Asp  Ile  Val  Val
               30                        35                       40

CTT  GGT  GTG  GAG  AAG  AAG  TCA  GTG  GCC  AAA  CTG  CAG  GAT  GAA  AGA  ACA    195
Leu  Gly  Val  Glu  Lys  Lys  Ser  Val  Ala  Lys  Leu  Gln  Asp  Glu  Arg  Thr
               45                       50                   55

GTG  CGG  AAG  ATC  TGT  GCT  TTG  GAT  GAC  AAC  GTC  TGC  ATG  GCC  TTT  GCA    243
Val  Arg  Lys  Ile  Cys  Ala  Leu  Asp  Asp  Asn  Val  Cys  Met  Ala  Phe  Ala
          60                        65                       70

GGC  CTC  ACC  GCC  GAT  GCA  AGG  ATA  GTC  ATC  AAC  AGG  GCC  CGG  GTG  GAG    291
Gly  Leu  Thr  Ala  Asp  Ala  Arg  Ile  Val  Ile  Asn  Arg  Ala  Arg  Val  Glu
75                       80                        85                        90

TGC  CAG  AGC  CAC  CGG  CTG  ACT  GTA  GAG  GAC  CCG  GTC  ACT  GTG  GAG  TAC    339
Cys  Gln  Ser  His  Arg  Leu  Thr  Val  Glu  Asp  Pro  Val  Thr  Val  Glu  Tyr
                    95                       100                      105

ATC  ACC  CGC  TAC  ATC  GCC  AGT  CTG  AAG  CAG  CGT  TAT  ACG  CAG  AGC  AAT    387
Ile  Thr  Arg  Tyr  Ile  Ala  Ser  Leu  Lys  Gln  Arg  Tyr  Thr  Gln  Ser  Asn
               110                       115                      120

GGG  CGC  AGG  CCG  TTT  GGC  ATC  TCT  GCC  CTC  ATC  GTG  GGT  TTC  GAC  TTT    435
Gly  Arg  Arg  Pro  Phe  Gly  Ile  Ser  Ala  Leu  Ile  Val  Gly  Phe  Asp  Phe
          125                      130                      135

GAT  GGC  ACT  CCT  AGG  CTC  TAT  CAG  ACT  GAC  CCC  TCG  GGC  ACA  TAC  CAT    483
Asp  Gly  Thr  Pro  Arg  Leu  Tyr  Gln  Thr  Asp  Pro  Ser  Gly  Thr  Tyr  His
     140                      145                      150
```

```
GCC TGG AAG GCC AAT GCC ATA GGC CGG GGT GCC AAG TCA GTG CGC GAG        531
Ala Trp Lys Ala Asn Ala Ile Gly Arg Gly Ala Lys Ser Val Arg Glu
155             160                 165                 170

TTC CTG GAG AAG AAC TAT ACT GAC GAA GCC ATT GAA ACA GAT GAT CTG        579
Phe Leu Glu Lys Asn Tyr Thr Asp Glu Ala Ile Glu Thr Asp Asp Leu
                175                 180                 185

ACC ATT AAG CTG GTG ATC AAG GCA CTC CTG GAA GTG GTT CAG TCA GGT        627
Thr Ile Lys Leu Val Ile Lys Ala Leu Leu Glu Val Val Gln Ser Gly
            190                 195                 200

GGC AAA AAC ATT GAA CTT GCT GTC ATG AGG CGA GAT CAA TCC CTC AAG        675
Gly Lys Asn Ile Glu Leu Ala Val Met Arg Arg Asp Gln Ser Leu Lys
        205                 210                 215

ATT TTA AAT CCT GAA GAA ATT GAG AAG TAT GTT GCT GAA ATT GAA AAA        723
Ile Leu Asn Pro Glu Glu Ile Glu Lys Tyr Val Ala Glu Ile Glu Lys
    220                 225                 230

GAA AAA GAA GAA AAC GAA AAG AAG AAA CAAAAGAAAG CATCATGATG              770
Glu Lys Glu Glu Asn Glu Lys Lys Lys
235                 240

AATAAAATGT CTTTGCTTGT AATTTTTAAA TTCATATCAA TCATGGATGA GTCTCGATGT      830

GTAGGCCTTT CCATTCCATT TATTCACACT GAGTGTCCTA CAATAAACTT CCGTATTTTT      890
```

( 2 ) INFORMATION FOR SEQ ID NO:2:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Tyr Asp Arg Ala Ile Thr Val Phe Ser Pro Asp Gly His Leu
 1               5                  10                  15

Phe Gln Val Glu Tyr Ala Gln Glu Ala Val Lys Lys Gly Ser Thr Ala
            20                  25                  30

Val Gly Val Arg Gly Arg Asp Ile Val Val Leu Gly Val Glu Lys Lys
        35                  40                  45

Ser Val Ala Lys Leu Gln Asp Glu Arg Thr Val Arg Lys Ile Cys Ala
    50                  55                  60

Leu Asp Asp Asn Val Cys Met Ala Phe Ala Gly Leu Thr Ala Asp Ala
65                  70                  75                  80

Arg Ile Val Ile Asn Arg Ala Arg Val Glu Cys Gln Ser His Arg Leu
                85                  90                  95

Thr Val Glu Asp Pro Val Thr Val Glu Tyr Ile Thr Arg Tyr Ile Ala
            100                 105                 110

Ser Leu Lys Gln Arg Tyr Thr Gln Ser Asn Gly Arg Arg Pro Phe Gly
        115                 120                 125

Ile Ser Ala Leu Ile Val Gly Phe Asp Phe Asp Gly Thr Pro Arg Leu
    130                 135                 140

Tyr Gln Thr Asp Pro Ser Gly Thr Tyr His Ala Trp Lys Ala Asn Ala
145                 150                 155                 160

Ile Gly Arg Gly Ala Lys Ser Val Arg Glu Phe Leu Glu Lys Asn Tyr
                165                 170                 175

Thr Asp Glu Ala Ile Glu Thr Asp Asp Leu Thr Ile Lys Leu Val Ile
            180                 185                 190

Lys Ala Leu Leu Glu Val Val Gln Ser Gly Gly Lys Asn Ile Glu Leu
        195                 200                 205
```

Ala Val Met Arg Arg Asp Gln Ser Leu Lys Ile Leu Asn Pro Glu Glu
210                 215                 220

Ile Glu Lys Tyr Val Ala Glu Ile Glu Lys Glu Lys Glu Glu Asn Glu
225                 230                 235                 240

Lys Lys Lys ( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

Gly Leu Pro Val Cys Ala Phe Ser Ser Ala Gly Pro Cys Ala Leu Arg
1                 5                   10                  15

Phe Thr Ser Ala
            20

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Modified-site
        ( B ) LOCATION: 1..20
        ( D ) OTHER INFORMATION: /note= "Mutations as follows: C at
            5 to S; G at 11 to A; P at 12 to A; C at 13 to S."

( x i ) SEQUENCE DESCRIPTION: SEQ ID NO:4:

Arg Leu Pro Ala Cys Leu Ala Ser Gly Ser Gly Pro Cys Cys Leu Val
1                 5                   10                  15

Phe Thr Cys Ala
            20

( 2 ) INFORMATION FOR SEQ ID NO:5:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (xi) SEQUENCE DESCRIPTION: SEQ ID NO:5:

```
Tyr Phe Lys Asp Cys Leu Phe Lys Asp Trp Glu Glu Leu Gly Glu Glu
1               5                   10                  15
Ile Arg Leu Lys Val Phe Val Leu Gly Gly Cys Arg His Lys Leu Val
            20              25                  30
Cys Ser Pro Ala Pro
        35
```

(2) INFORMATION FOR SEQ ID NO:6:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Modified-site
        (B) LOCATION: 1..35
        (D) OTHER INFORMATION: /note= "Mutations as follows: W at
            10 to R; F at 22 to Y; G at 26 to V; C at 27 to S;
            R at 28 to Q; H at 29 to D."

(xi) SEQUENCE DESCRIPTION: SEQ ID NO:6:

```
Tyr Ile Lys Asp Gln Leu Leu Thr Lys Trp Glu Glu Gly Ser Ile Asp
1               5                   10                  15
Pro Arg Leu Ser Ile Phe Leu Leu Gly Gly Cys Arg His Lys Cys Met
            20              25                  30
Arg Leu Leu
        35
```